(12) United States Patent
Roethlisberger et al.

(10) Patent No.: US 9,393,064 B2
(45) Date of Patent: Jul. 19, 2016

(54) CAM LOCK

(71) Applicant: DEPUY SYNTHES PRODUCTS, INC., Raynham, MA (US)

(72) Inventors: Stefan Roethlisberger, Solothurn (CH); Daniel Andermatt, Solothurn (CH)

(73) Assignee: DePuy Synthes Products, Inc., Raynham, MA (US)

( * ) Notice: Subject to any disclaimer, the term of this patent is extended or adjusted under 35 U.S.C. 154(b) by 486 days.

(21) Appl. No.: 13/753,883

(22) Filed: Jan. 30, 2013

(65) Prior Publication Data

US 2014/0214101 A1 Jul. 31, 2014

(51) Int. Cl.
*A61F 2/46* (2006.01)
*A61B 17/88* (2006.01)
*A61B 17/17* (2006.01)

(52) U.S. Cl.
CPC ......... *A61B 17/8872* (2013.01); *A61B 17/1725* (2013.01)

(58) Field of Classification Search
CPC .............. Y10T 403/59; Y10T 403/608; Y10T 403/321; Y10T 24/44017; Y10T 24/44026; A61B 17/8872; A61B 17/1725
See application file for complete search history.

(56) References Cited

U.S. PATENT DOCUMENTS

| | | | |
|---|---|---|---|
| 6,039,739 A | 3/2000 | Simon | |
| 6,481,790 B2 * | 11/2002 | Cheng | 297/153 |
| 6,620,195 B2 | 9/2003 | Goble et al. | |
| 7,229,448 B2 | 6/2007 | Goble et al. | |
| 7,311,710 B2 | 12/2007 | Zander | |
| 7,963,984 B2 | 6/2011 | Goble et al. | |
| 2004/0059329 A1 | 3/2004 | Zander | |

FOREIGN PATENT DOCUMENTS

| | | |
|---|---|---|
| EP | 0 948 936 | 10/1999 |
| EP | 1 386 588 | 2/2004 |
| EP | 1854611 A1 | 11/2007 |

(Continued)

OTHER PUBLICATIONS

Written Opinion of the International Searching Authority, Internationl Application No. PCT/US2014/011665; Date of Mailing Jul. 15, 2014, 7 pages.

(Continued)

*Primary Examiner* — Christopher Beccia
*Assistant Examiner* — Diana S Jones
(74) *Attorney, Agent, or Firm* — Wayne C. Jaeschke, Jr.

(57) ABSTRACT

An aiming device includes a body extending longitudinally from a first end to a second end and including a first body opening extending laterally therethrough along a first axis, the first body opening being sized and shaped to receive a device therein, the first end of the body including a coupling for coupling the body to an implantable device in an aiming configuration in which the first body opening is aligned with a corresponding first implant opening extending through the implantable device so that a device inserted through the first body opening in the body will pass along an axis of the first implant opening and a lock releasably coupled to the body and movable relative thereto between an unlocked and a locked configuration, the lock including an engaging portion extending into the first body opening in the locked configuration to engage an outer surface of a device received therein to lock the device in a desired position within the first body opening.

31 Claims, 18 Drawing Sheets

(56) References Cited

FOREIGN PATENT DOCUMENTS

| | | | |
|---|---|---|---|
| EP | 2548523 | A1 | 1/2013 |
| FR | 2934145 | A1 | 1/2010 |
| WO | WO 2011/046784 | A1 | 4/2011 |
| WO | WO 2011/050842 | A1 | 5/2011 |

OTHER PUBLICATIONS

Notification of Transmittal of the International Serach Report and Written Opinion of the International Searching Authority, Internationl Application No. PCT/US2014/011665; Date of Mailing Jul. 15, 2014, 7 pages.

\* cited by examiner

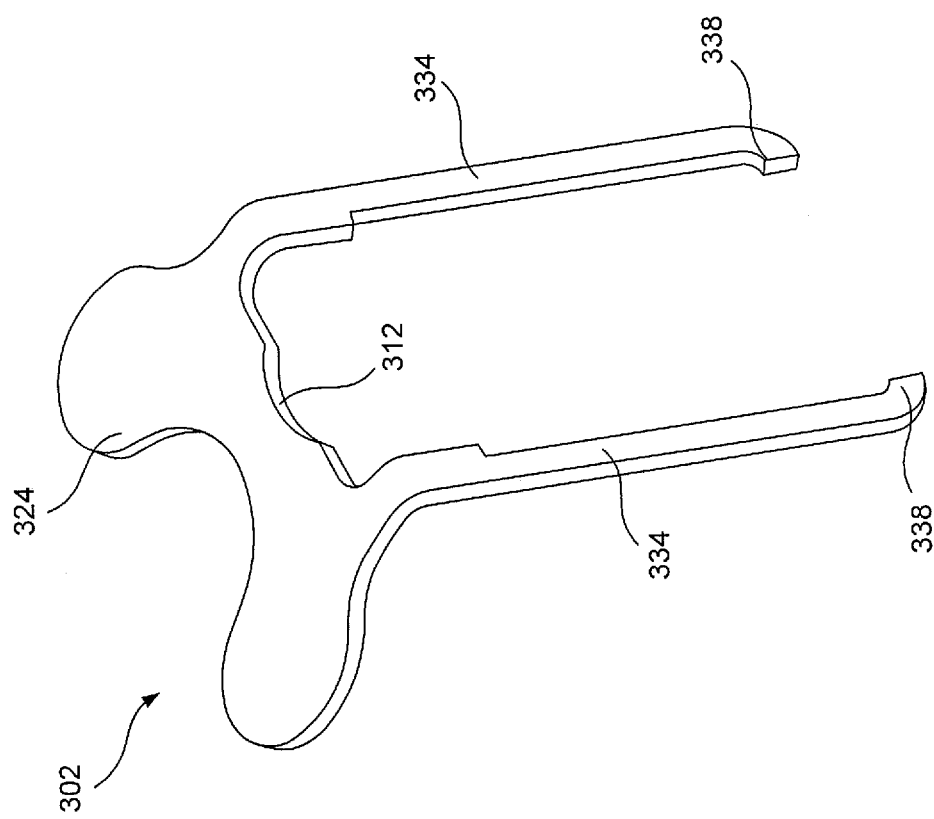

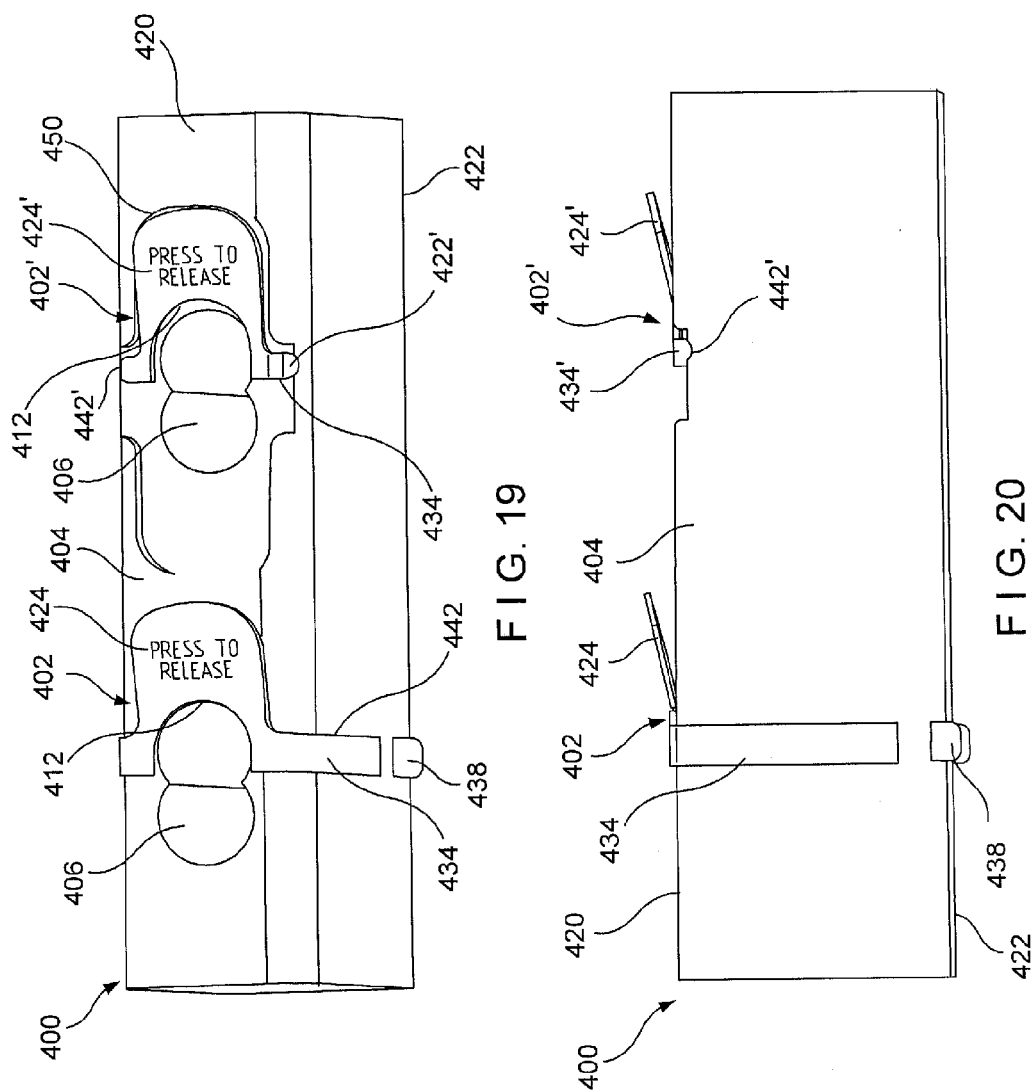

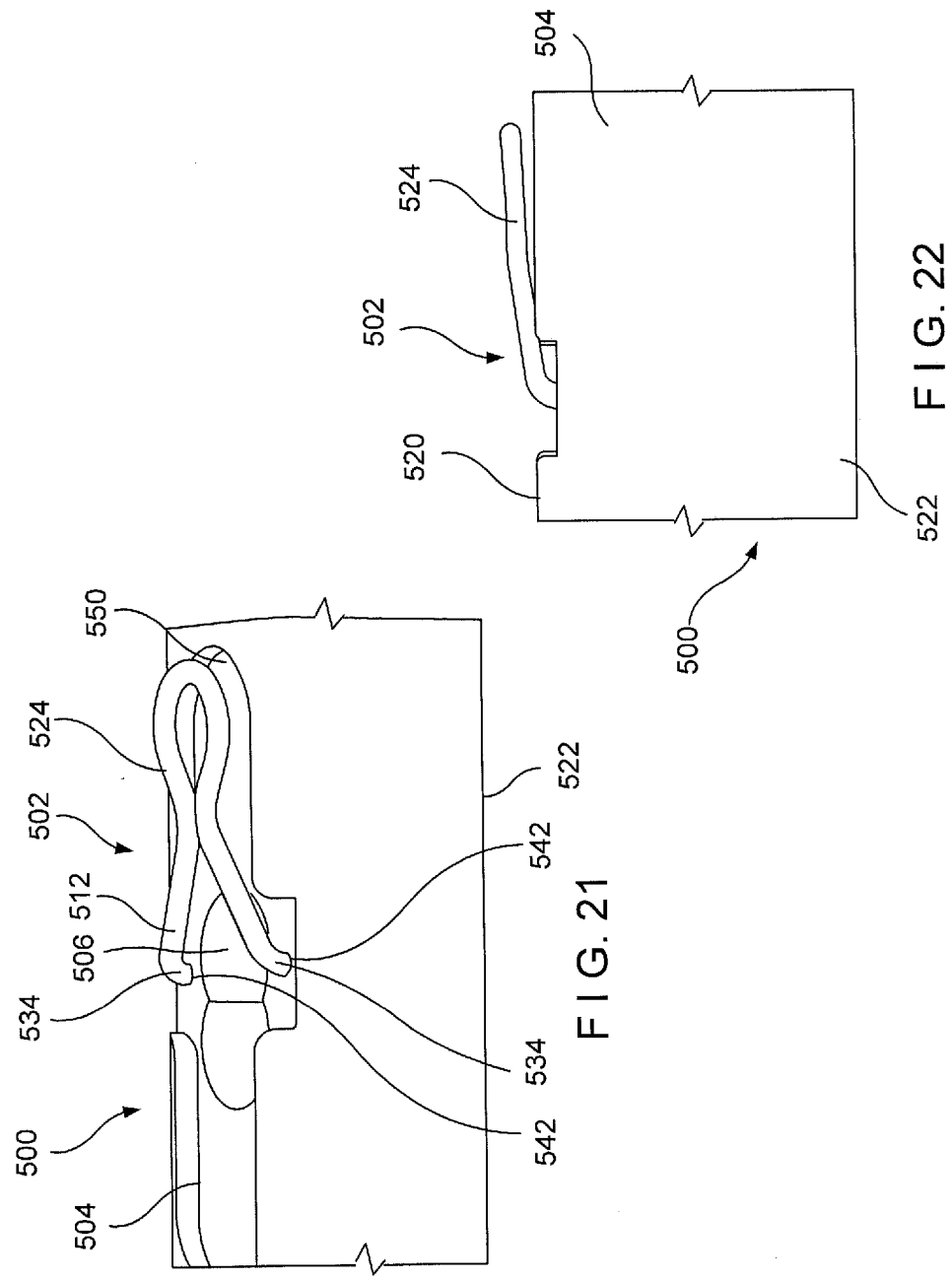

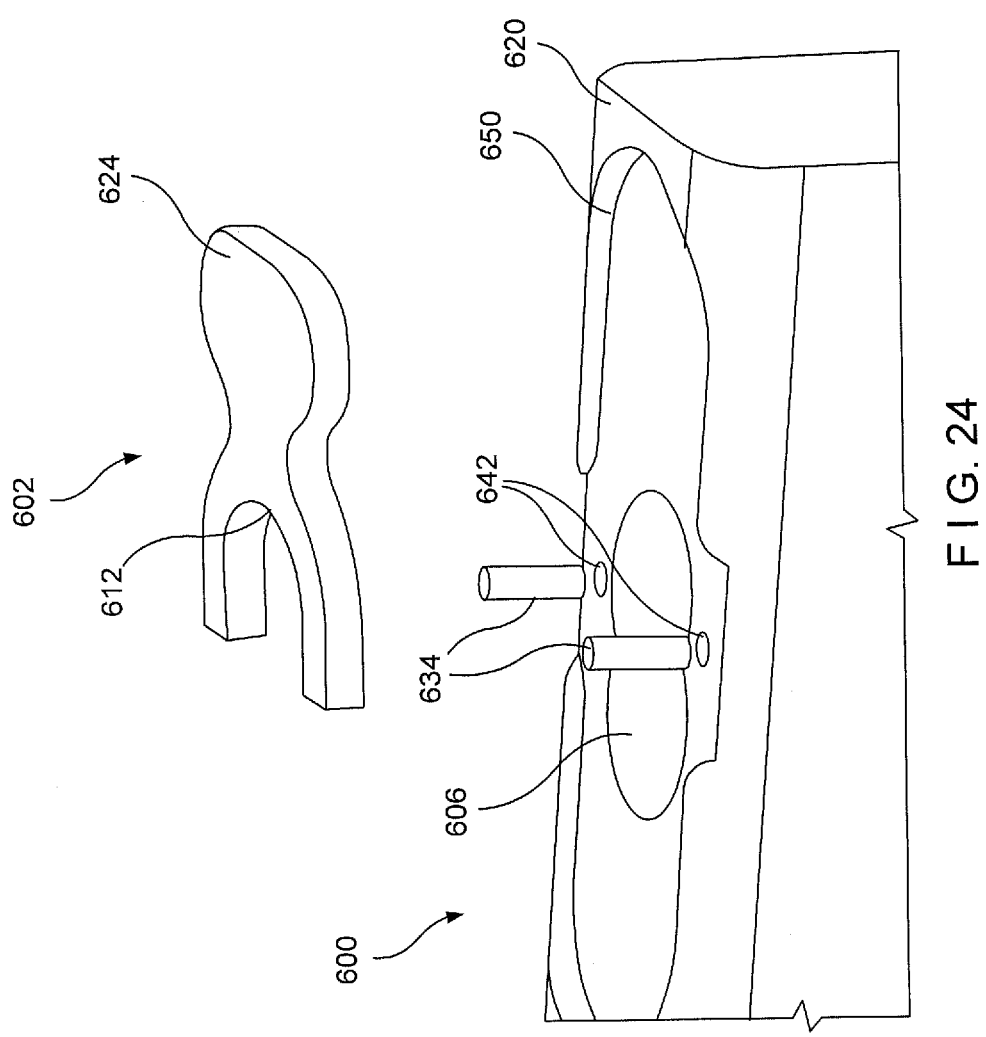

CAM LOCK

BACKGROUND

Intramedullary nails are often inserted into medullary canals of long bones to fix fractures. Once an intramedullary nail has been inserted into a medullary canal, other bone fixation elements may be inserted laterally through the bone into openings of the intramedullary nail to further fix the bone and/or to fix the nail to the bone. For example, a helical screw or other implant may be inserted through an opening of the intramedullary nail and into a head portion of the bone to fix fractures of the head and/or neck portion of the bone. As the nail is no longer visible once it has been inserted into a bone, an aiming device may be coupled to the nail during an insertion procedure to facilitate the placement of these fixation elements through the bone and into the desired holes in the nail. The nail may be coupled to the aiming device via, for example, an insertion handle. An aiming device may, for example, include a plurality of holes positioned to guide fixation elements through the bone and into openings of the intramedullary nail. The aiming device may be coupled to, for example, a proximal end of the intramedullary nail in an alignment in which each of the holes extending through the aiming device aligns with a corresponding one of the openings of the intramedullary nail so that a protective sleeve and/or a drilling device inserted through a hole of the aiming device is aligned with the corresponding one of the openings of the intramedullary nail. In some cases, it may be desirable to fix the protective sleeve or tool within the opening.

SUMMARY OF THE INVENTION

The present invention is directed to an aiming device, comprising a body extending longitudinally from a first end to a second end and including a first body opening extending laterally therethrough along a first axis, the first body opening being sized and shaped to receive a device therein, the first end of the body including a coupling for coupling the body to an implantable device in an aiming configuration in which the first body opening is aligned with a corresponding first implant opening extending through the implantable device so that a device inserted through the first body opening in the body will pass along an axis of the first implant opening and a lock releasably coupled to the body and movable relative thereto between an unlocked and a locked configuration, the lock including an engaging portion extending into the first body opening in the locked configuration to engage an outer surface of a device received therein to lock the device in a desired position within the first body opening.

BRIEF DESCRIPTION OF THE DRAWINGS

FIG. 18 shows a perspective view of a lock according to the device of FIG. 17;

FIG. 19 shows a perspective view of a portion of an aiming device according to a fourth exemplary embodiment of the present invention;

FIG. 20 shows a side view of the aiming device of FIG. 19;

FIG. 21 shows a perspective view of a portion of an aiming device according to a fifth exemplary embodiment of the present invention;

FIG. 22 shows a side view of the aiming device of FIG. 21;

FIG. 24 shows a side view of the aiming device of FIG. 23.

DETAILED DESCRIPTION

Figure 1:
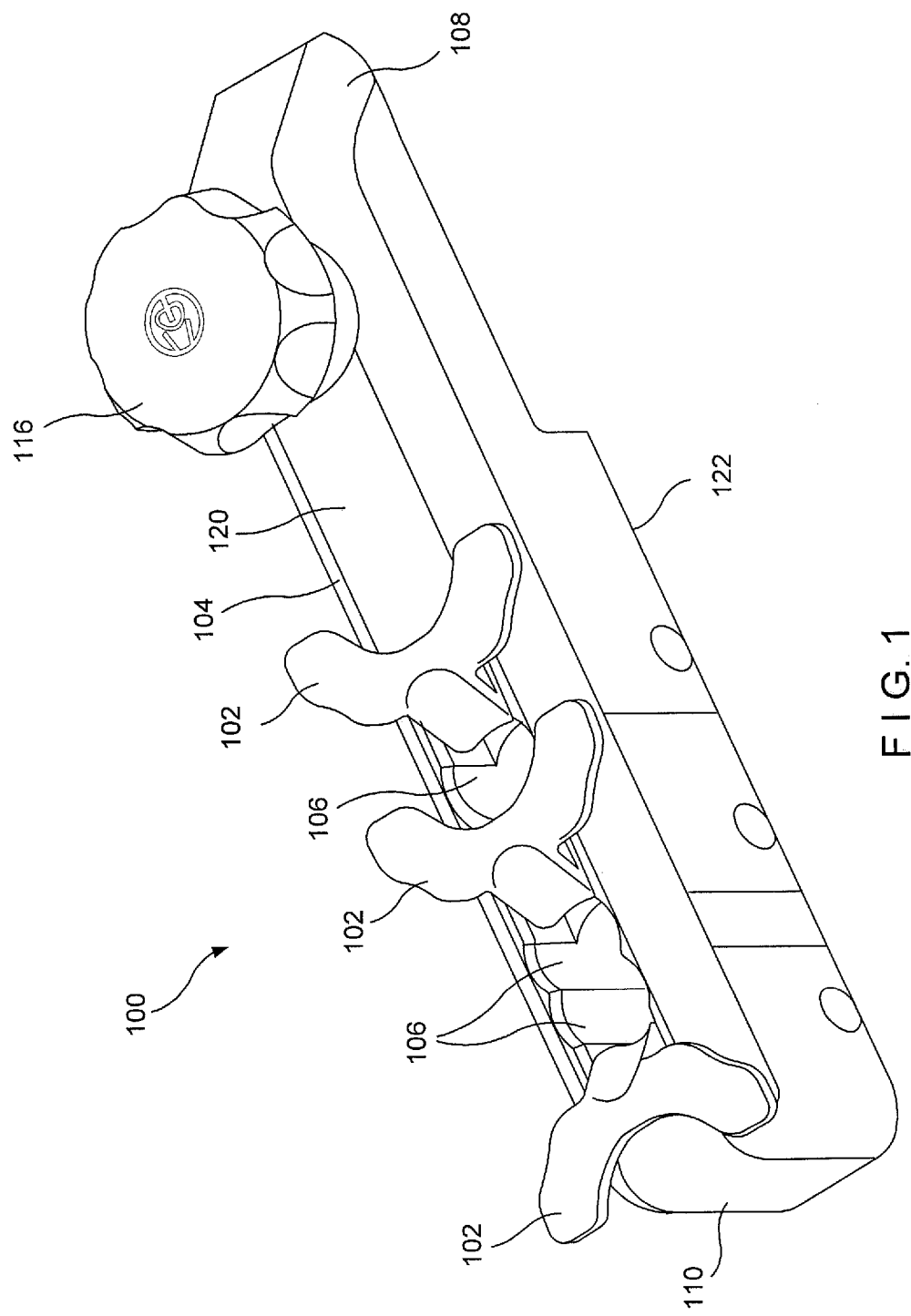
FIG. 1 shows a perspective view of an aiming device according to a first exemplary embodiment of the present invention.

The present invention may be further understood with reference to the following description and the appended drawings, wherein like elements are referred to with the same reference numerals. The present invention relates to bone treatment devices and, in particular, to an aiming device for guiding bone fixation elements and/or other tools into an opening of a bone treatment device such as an intramedullary nail. Exemplary embodiments of the present invention describe an aiming device comprising a locking cam for locking a sleeve and/or drill tool within a hole of the aiming device and in alignment with the opening of the bone treatment device. It should be noted that the terms "proximal" and "distal," as used herein, are intended to refer to a direction toward (proximal) and away from (distal) a surgeon or other user of the device.

A shown in FIGS. 1-7, an aiming device 100 according to an exemplary embodiment of the present invention includes a lock 102 coupled to a body 104 to fix a device 114 such as a protective sleeve or drilling device within an opening 106 of the body 104. The lock 102 is movable relative to the body 104 between an unlocked configuration, in which no portion of the lock 102 extends into the opening 106, and a locked configuration in which an engaging portion 112 of the lock 102 extends into the opening 106 to engage the device 114, locking the device 114 within the opening 106. The body 104 extends longitudinally from a first end 108 to a second end 110 and includes the opening 106 extending laterally therethrough. The opening 106 is positioned along the body 104 such that when the first end 108 is coupled to a bone fixation device such as, for example, an intramedullary nail, the opening 106 extends along an opening axis aligned with a hole extending laterally through the intramedullary nail. The lateral hole is configured to receive a further fixation device such as, for example, a locking screw to lock the intramedullary nail within the bone and/or a helical screw extending through a head portion of the bone to provide fixation of the head portion. It will be understood by those of skill in the art that the aiming device 100 may be coupled to the intramedullary nail via, for example, an insertion handle for inserting the intramedullary nail into the bone. The first end 108 of the body 104 of the aiming device 100 may be coupled to the insertion handle via a knob 116. Thus, a device 114 such as a protective sleeve inserted into the opening 106 will guide drills and/or other tools into the bone along an axis of the nail hole. Although the aiming device 100 will be described and shown with regard to an intramedullary nail, it will be understood by those of skill in the art that the lock 102 may be used in any aiming device 100 in which a device 114 or tool is inserted through an opening thereof. It will also be understood by those of skill in the art that although the lock 102 is described with respect to a single opening 106, the body 104 may include a plurality of openings 106 to corresponding to a plurality of holes extending through the intramedullary nail. One or more openings 106 may overlap one another, as shown in FIG. 1. In addition, the aiming device 100 may include more than one lock 102, such as, for example, a lock 102 for each of a plurality of openings 106.

Figure 2:
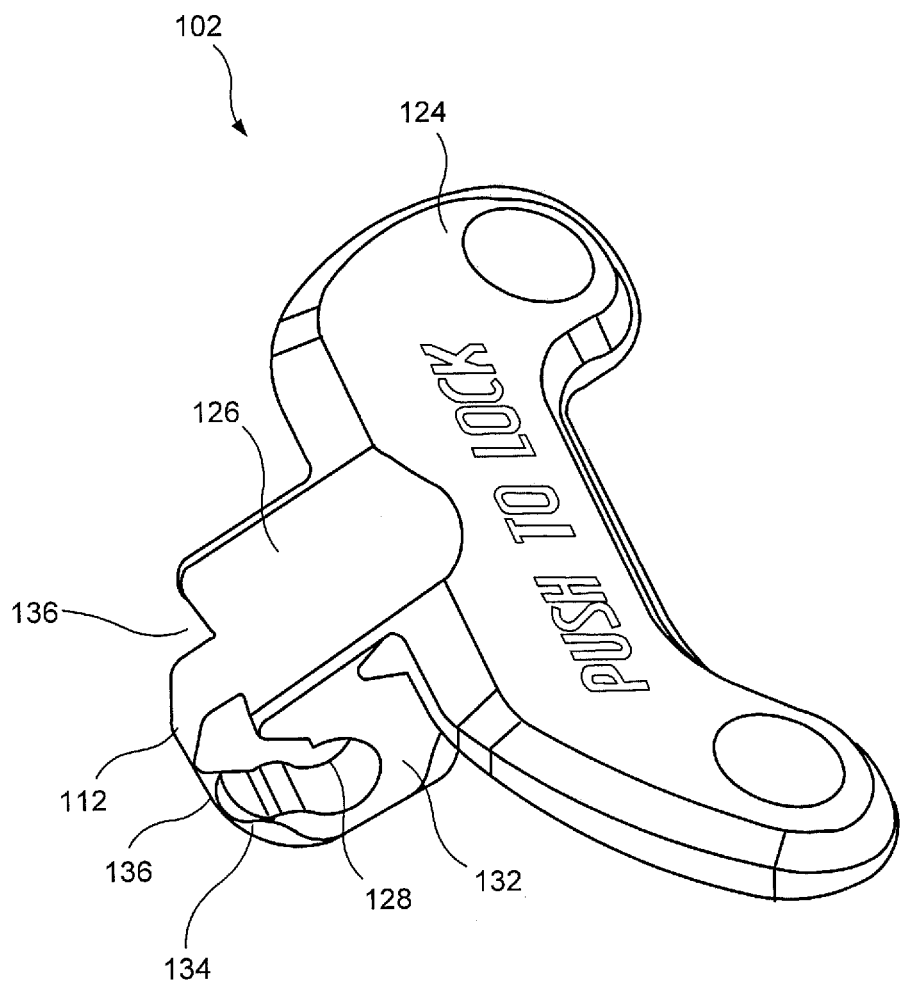
FIG. 2 shows a perspective view of a lock according to the aiming device of FIG. 1.
Figure 4:
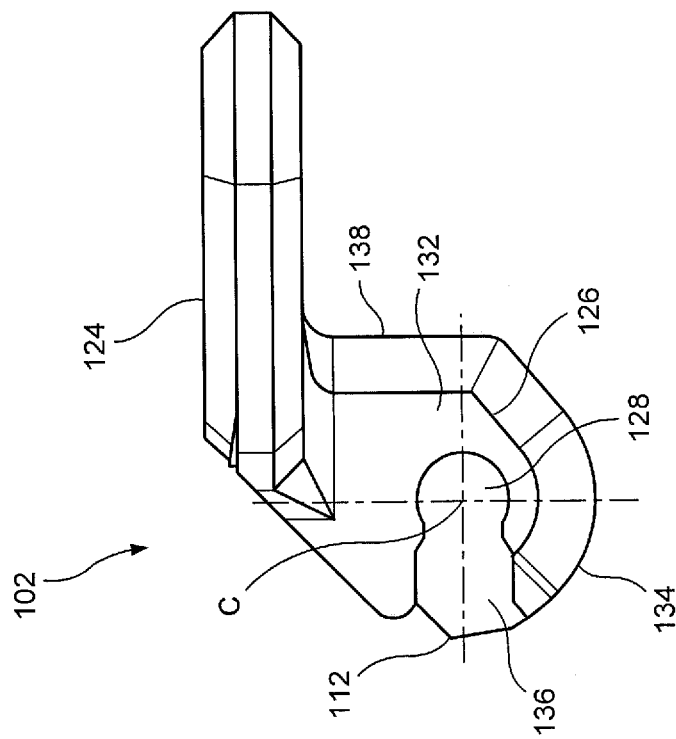
FIG. 4 shows a side view of the lock of FIG. 2.
Figure 3:
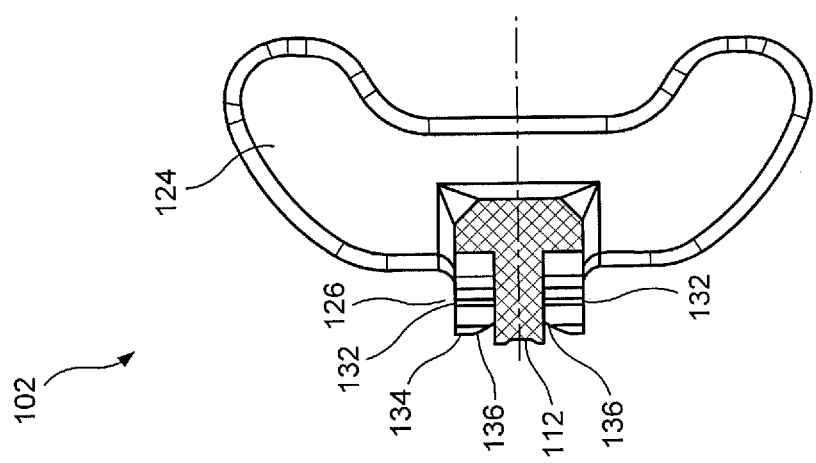
FIG. 3 shows a top view of the lock of FIG. 2.

The lock 102 may be coupled to the body 104 via a pin 130. As shown in FIGS. 2-4, the lock 102 includes a tab 124 extending from a locking member 126. The locking member 126 includes a pair of planar surfaces 132 connected to one another via a connecting surface 134. A distance between the planar surfaces 132 defines a width of the locking member 126. The locking member 126 also includes a hole 128 extending therethrough from a first one of the planar surfaces 132 to a second one of the planar surfaces 132 along a central axis C. The hole 128 is sized and shaped to receive the pin 130 therein such that the lock 102 pivots about the pin 130 and the central axis C between the unlocked and locked configurations. The connecting surface 134 may be rounded about the central axis C such that the locking member 126 is permitted to pivot about the central axis C within the body 104. An engaging portion 112 protrudes radially outward from the connecting surface 134 such that when the lock 102 is moved to the locked configuration, the engaging portion 112 extends into the opening 106 to engage an outer surface of a device 114 inserted through the opening 106. The connecting surface 134 may also include a substantially planar locking surface 138. The locking surface 138 may be positioned proximate the tab 124 to interface with a portion of the body 104 when the lock 102 is in the locked configuration. The locking member 126 may also include a pair of grooves 136 extending along the planar surfaces 132 from the engaging portion 112 toward the central axis C such that a width of the engaging portion 112 (e.g., a distance between the grooves 136) is smaller than the width of a remaining portion of the locking member (e.g., the distance between the planar surfaces 132).

The tab 124 extends laterally away from the locking member 126 and is sized and shaped to be gripped and/or pressed by a user of the device 100. In one exemplary embodiment, the tab 124 may be wing-shaped. It will be understood by those of skill in the art, however, that the tab 124 may have any of a variety of shapes so long as the tab 124 may be grasped by the user to move the lock 102 between the receiving and locked configurations.

Figure 5A:
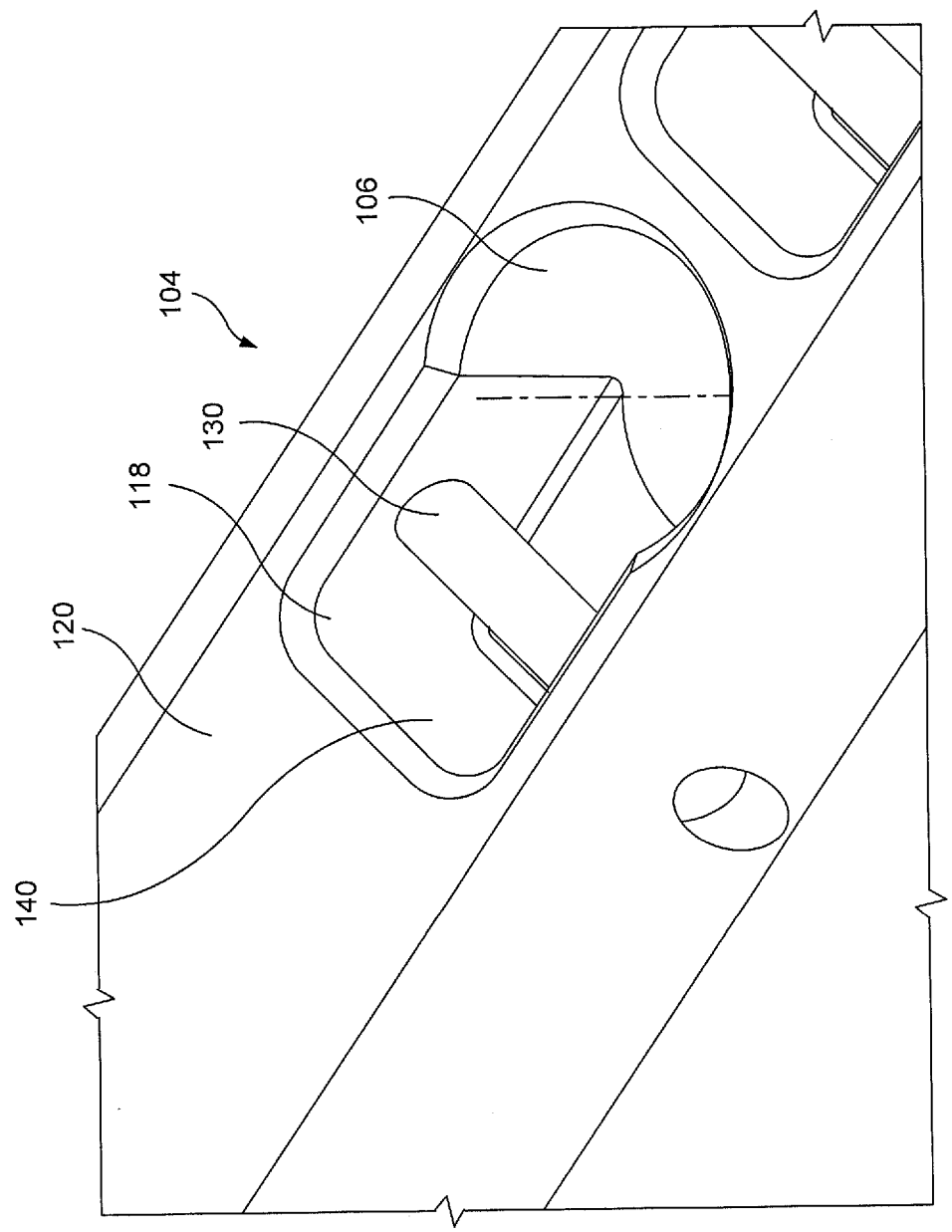
FIG. 5A shows an enlarged view of a portion of a body of the aiming device of FIG. 1.
Figure 5B:
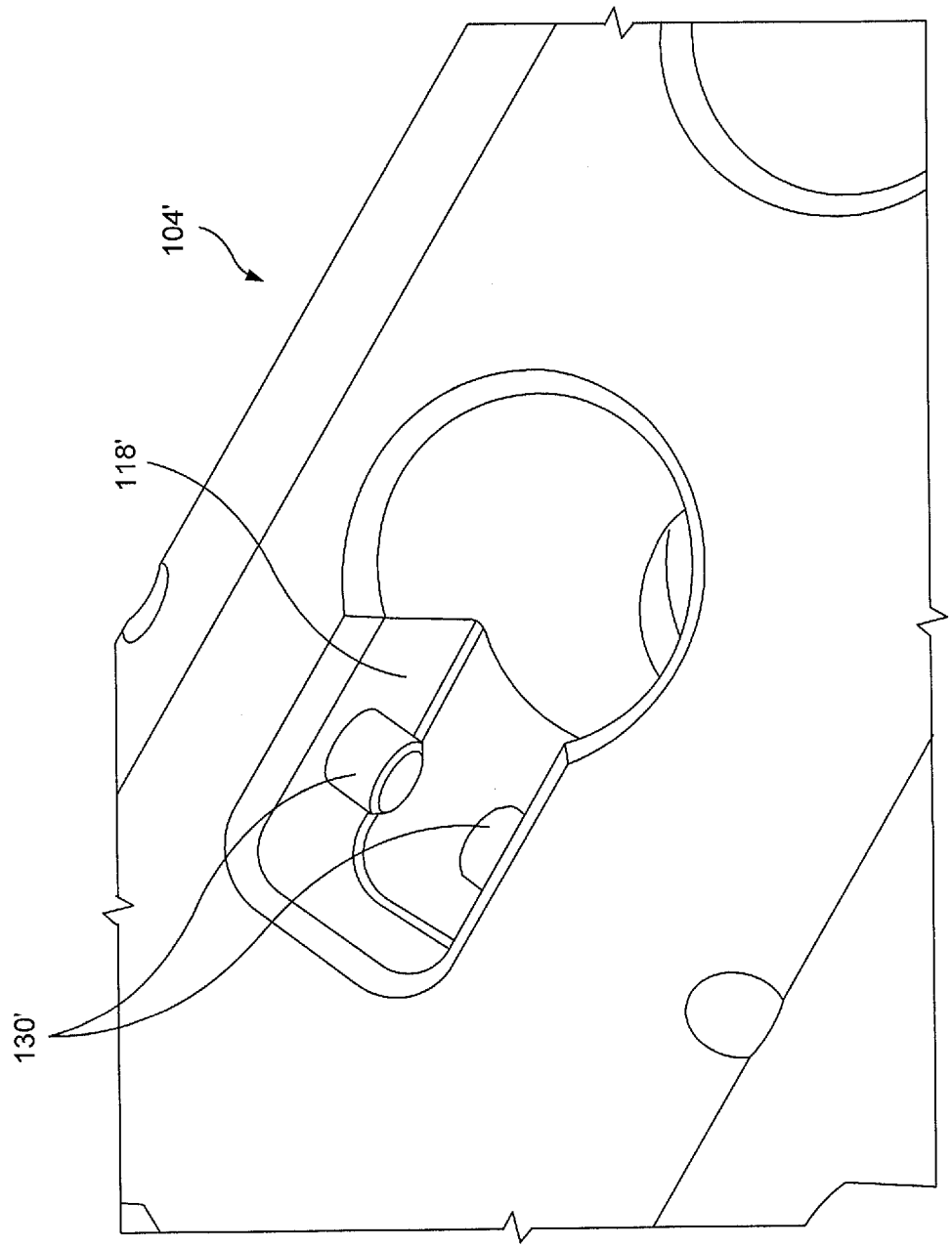
FIG. 5B shows an enlarged view of a portion of a body of an aiming device according to another embodiment of the present invention.

The opening 106 extends laterally through the body 104 from a proximal surface 120 to a distal surface 122 thereof. The opening 106 is sized and shaped to receive a device 114 therein. The body 104 further includes a recess 118 extending longitudinally along the proximal surface 120 from the opening 106 through a portion of the body 104. As shown in FIG. 5A, the recess 118 is positioned along the body 104 to overlap with a portion of the opening 106 and is sized and shaped to receive the locking member 126 of the lock 102 therein. The pin 130 extends through the recess 118 and the hole 128 of the lock 102 such that the locking member 126 is pivotable about the pin 130 within the recess 118. In another embodiment, as shown in FIG. 5B, the lock 102 may be coupled to a body 104' via a pair of pins 130'. The pins 130' are positioned on opposing sidewalls of a recess 118' and extend into opposite openings of the hole 128 of the lock 102. It will be understood by those of skill in the art, however, that rather than the hole 128 extending through an entire width of the locking member 126, the lock 102 may include a pair of recesses extending into each of the planar surfaces 132 to accommodate the pair of pins 130 therein.

Figure 6:
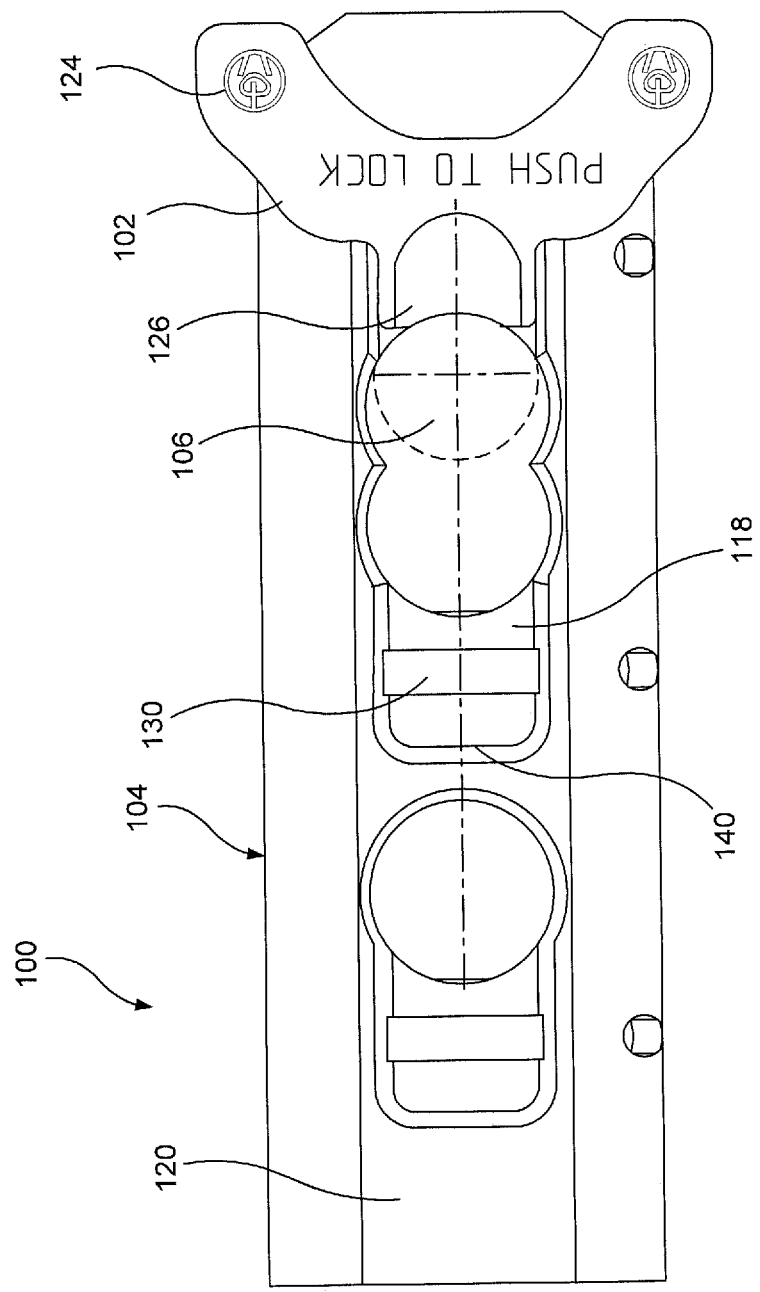
FIG. 6 shows a top view of the aiming device of FIG. 1, in an unlocked configuration.
Figure 7:
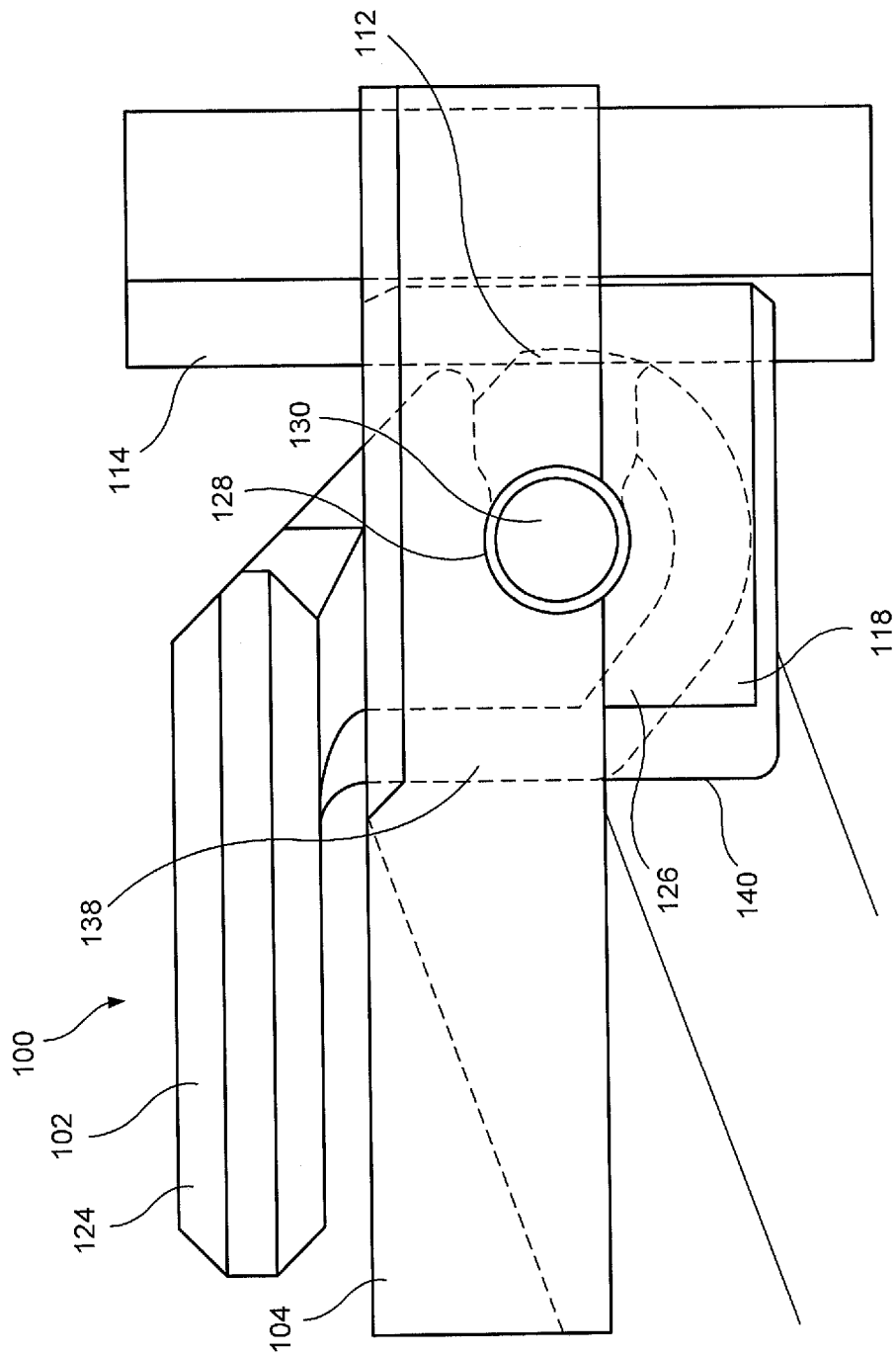
FIG. 7 shows a side view of the aiming device of FIG. 1, in a locked configuration.

In the unlocked configuration, as shown in FIG. 6, the tab 124 extends away from the proximal surface 120 of the body 104 and the engaging portion 112 does not extend into the opening 106 such that the opening 106 is clear to receive the sleeve 114, or other tool, therein. In the locked configuration, the tab 124 is moved toward the proximal surface 120 to pivot the lock 102 about the pin 130, moving the engaging portion 112 of the locking member 126 into the opening 106, as shown in FIG. 7. The engaging portion 112 extends into an exterior surface of a sleeve 114 received within the opening 106 to fix the sleeve 114 therein. The locking surface 138 also engages a substantially planar lateral surface 140 of the recess 118 to retain the lock 102 relative to the body 104 in the locked configuration. In the locked configuration, the tab 124 according to this embodiment extends substantially parallel to the proximal surface 120. Once the aiming device 100 has been used, as desired, the lock 102 may be moved back to the unlocked configuration to remove the device 114 therefrom. To unlock the lock 102, the user moves the tab 124 away from the proximal surface 120, drawing the locking surface 138 out of engagement with the lateral surface 140 of the recess 118 and moving the engaging portion 112 out of the opening 106 to release the device 114.

The lock 102 may be decoupled from the body 104. In one exemplary embodiment in which the device 100 includes a single pin 130, the pin 130 may be removed to decouple the lock 102 from the body 104. In another exemplary embodiment in which the device 100 includes a pair of pins 130', the lock 102 may be unclipped from the pins 130' via the grooves 136 extending along the planar surfaces 132 thereof. The lock 102 may be moved such that the pins 130 are slid along the grooves 136 and the lock 102 is decoupled from the body 104'. The lock 102 and the body 104' may be decoupled such that the lock 102 may be replaced, when necessary, and the body 104' and the lock 102 cleaned, as needed. The lock 102 may be recoupled to the body 104' by sliding the pins 130 through the grooves 136 of the lock 102 until the pins 130' are received within the hole 128 or opposing recesses thereof. It will be understood by those of skill in the art that the pins 130' may be snapped into the openings of the hole 128 or recesses to prevent the lock 102 from being inadvertently decoupled from the body 104. The lock 102 may be formed of a radiolucent material such that the opening 106 of the aiming device 100 may be clearly imaged and viewed to guide the sleeve 114 and/or other tools therethrough.

As shown in FIGS. 8-16, an aiming device 200 according to a second exemplary embodiment of the present invention is substantially similar to the device 100 described above, comprising a lock 202 coupled to a body 204 to fix a device 214 such as a guiding sleeve or other tool within an opening 206 thereof Similarly to the device 100, the lock 202 is movable between an unlocked and a locked configuration. The lock 202, however, includes a tab 224 and a clip 226, which is biased in a locked configuration such that the tab 224 of the lock 202 must be pressed to move the clip 226 to the unlocked configuration, permitting the device 214 to be inserted through the opening 206. Once the device 214 has been inserted into the opening 206, as desired, the tab 224 may be released to revert the clip 226 to the biased position, locking the device 214 within the opening 206.

Figure 8:
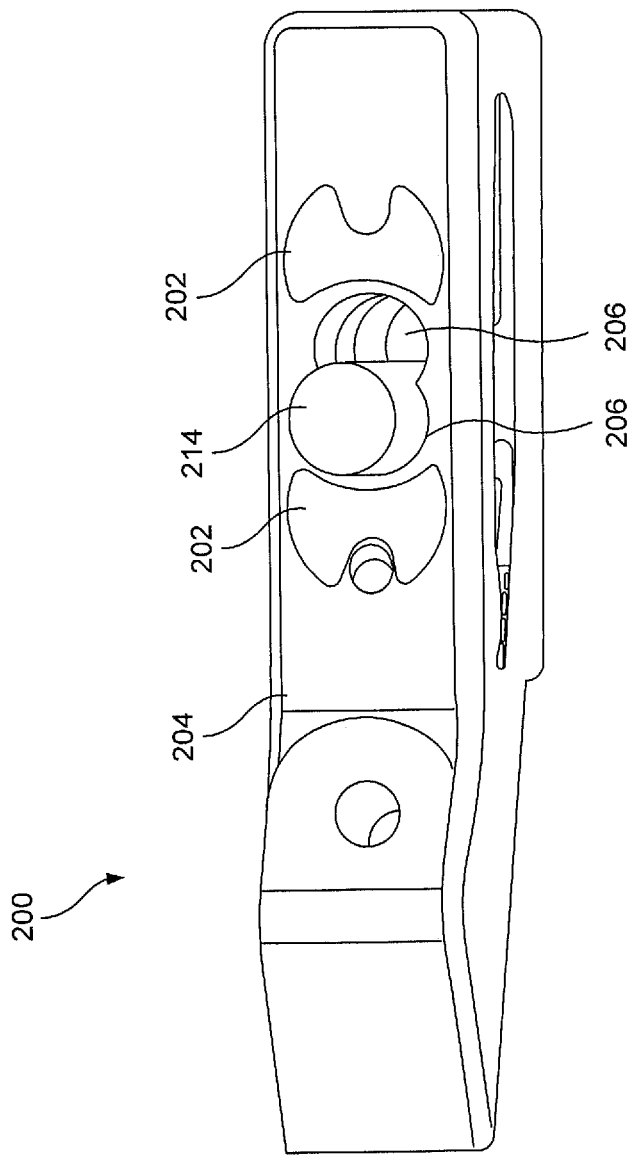
FIG. 8 shows a perspective view of an aiming device according to a second exemplary embodiment of the present invention.
Figure 9:
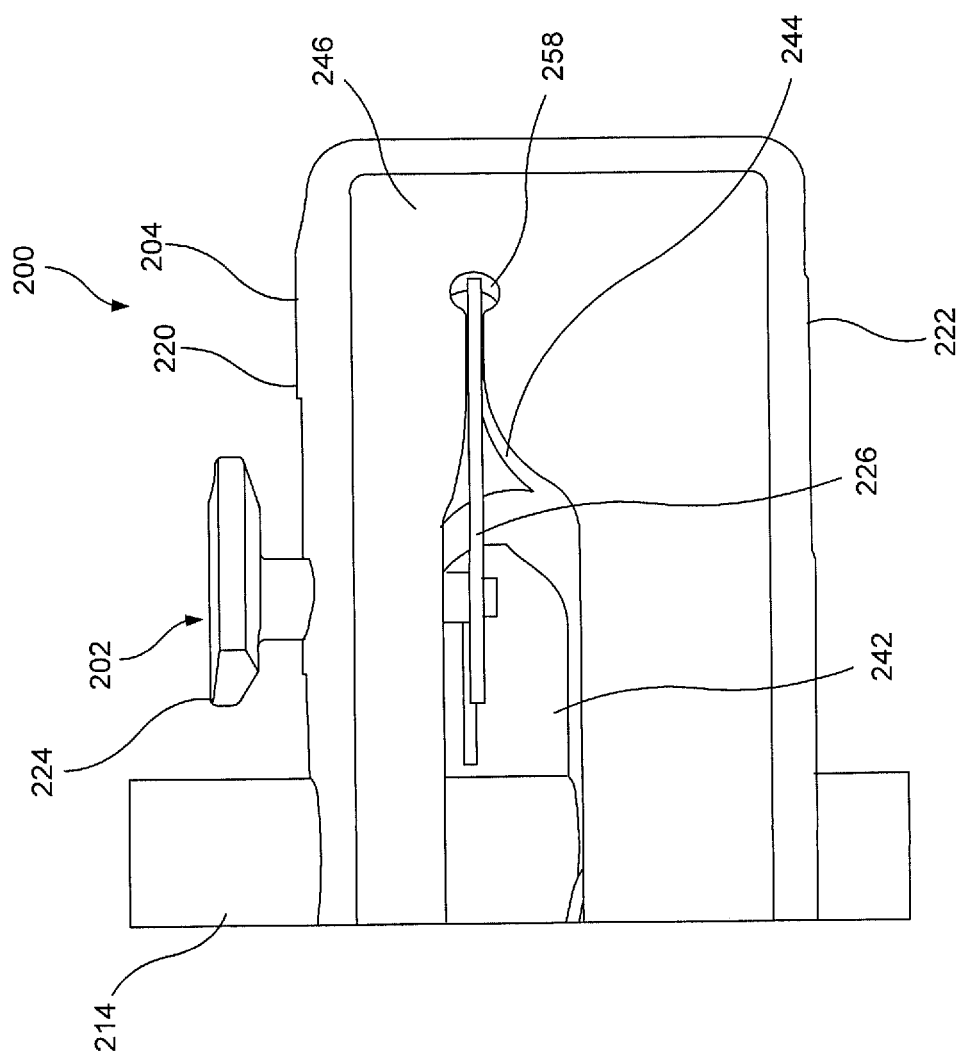
FIG. 9 shows a side view of the device of FIG. 8.
Figure 10:
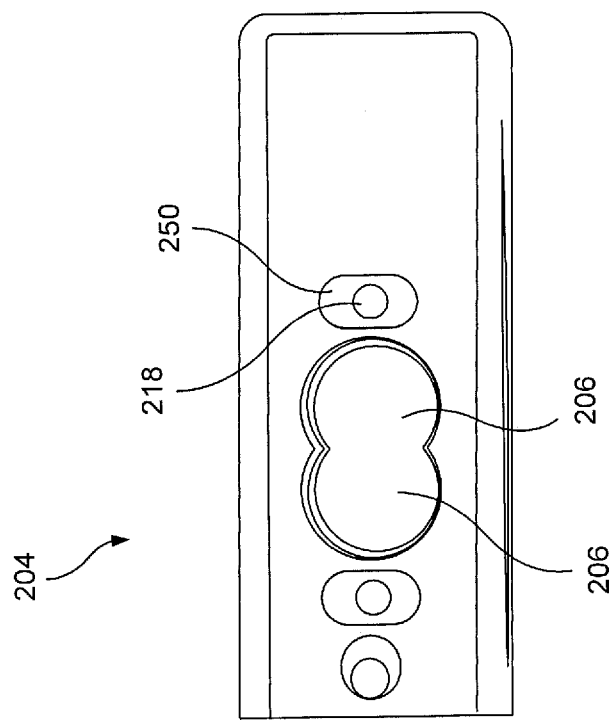
FIG. 10 shows a top view of a body of the device of FIG. 8.

Similarly to the body 104, as shown in FIGS. 8-10, the body 204 may be coupled to a bone fixation device and may include on or more openings 206 which, when the aiming device 100 is coupled to the bone fixation device, correspond to holes of the bone fixation device. The body 204 includes a longitudinal slot 242 passing through the opening 206 between proximal and distal surfaces 220, 222 thereof. The body 204 also includes a groove 244 on opposing lateral sides 246 of the body 204, the lateral sides 246 connecting the proximal and distal surfaces 220, 222. The grooves 244 are in communication with the longitudinal slot 242 and are sized and shaped to accommodate a portion of the clip 226. In particular, the grooves 244 include a recessed end 258 for receiving a locking portion 238 of the clip 226 to hold a portion of the clip 226 within the longitudinal slot 242. The grooves 244 are also shaped to permit the clip 226 to be moved between the locked and unlocked configurations—e.g., the portion of the clip 226 received within the longitudinal slot 242 is laterally movable therewithin.

The body 204 further includes a hole 218 extending therethrough from the proximal surface 220 to the distal surface 222 and sized and shaped to receive a stem portion 248 of the lock 202, which connects the tab 224 to the clip 226. The body 204 may also include a recessed portion 250 on the proximal surface 220 along a portion thereof surrounding the hole 218. The recessed portion 250 has a non-circular shape such that a correspondingly shaped extension 252 of the tab 224 is received therein to prevent the tab 224 from being rotated relative to the body 224. The hole 218 and the recessed portion 250 are longitudinally spaced apart from the opening 206.

Figure 11:
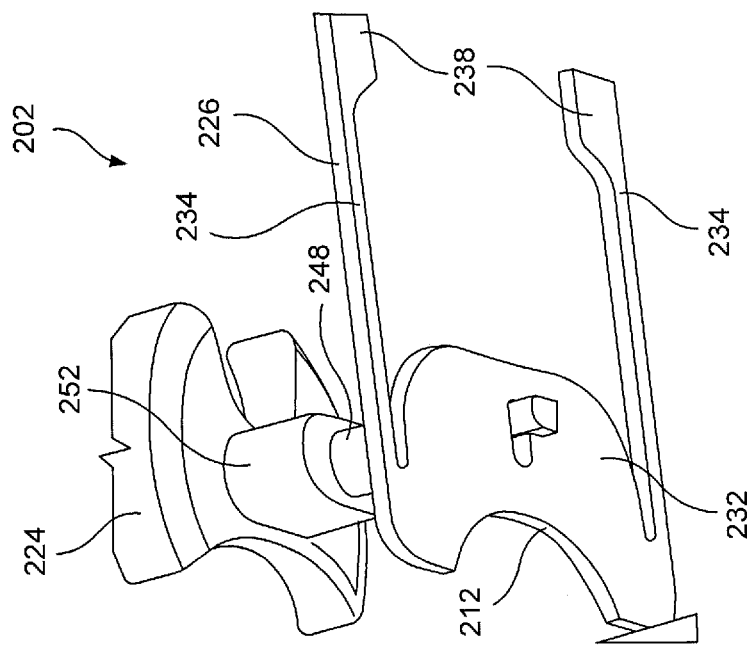
FIG. 11 shows a perspective view of a lock according to the device of FIG. 8.
Figure 12:
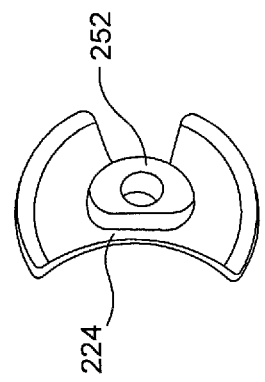
FIG. 12 shows a perspective view of a lever portion of the lock of FIG. 11.
Figure 13:
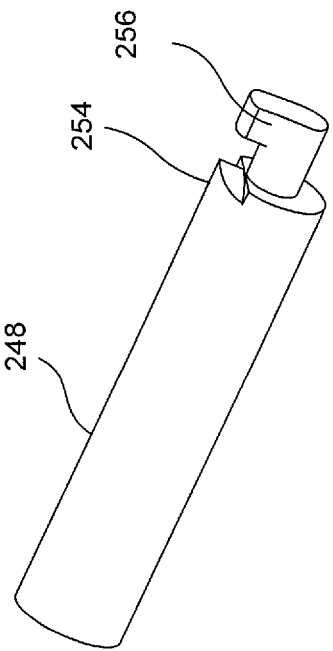
FIG. 13 shows a perspective view of a stem portion of the lock of FIG. 11.

As shown in FIG. 11, the lock 202 includes the tab 224 connected to the clip 226 via the stem portion 248. The lock 202 is coupled to the body 204 such that a portion of the clip 224 is received within the longitudinal slot 242 to engage a device 214 received within the opening 206. As shown in FIG. 12, the tab 224 is sized and shaped to permit a user to press the lock 202 via the tab 224 to move the lock 202 between the locked and unlocked configurations. The tab 224 includes the extension 252 extending distally therefrom to be received within the recesses portion 250 of the body 204. As shown in FIG. 13, the stem 248 extends longitudinally from the extension 252 to a distal end 254 including an L-shaped tip 256. The L-shaped top 256 couples the stem 248 to the clip 226.

Figure 14:
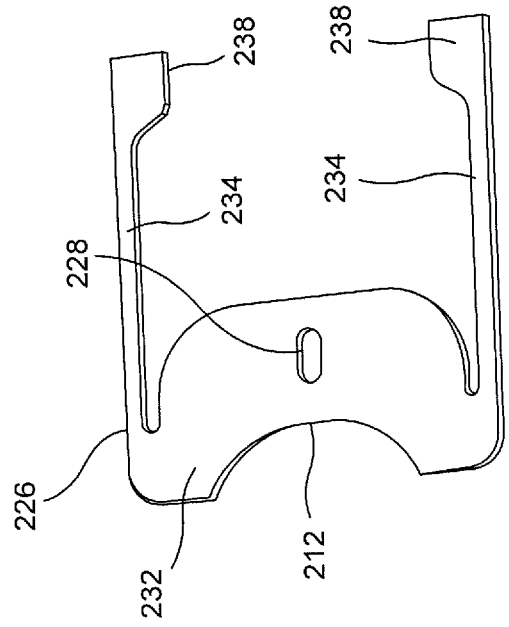
FIG. 14 shows a perspective view of a clip portion of the lock of FIG. 11.

As shown in FIG. 14, the clip 226 according to this embodiment includes a clip body 232 and arms 234 extending therefrom. The clip body 232 is received within the longitudinal slot 242 and includes an engaging portion 212 to engage a device 214 passed through the opening 206. The engaging portion 212 is sized and shaped to correspond to an exterior surface of the device 214. For example, the engaging portion 212 may be defined as a curved recess to accommodate a cylindrical device 214. The clip body 232 may include an elongated hole 228 for receiving the L-shaped tip 256 of the stem 248 such that the tab 224 is coupled to the clip 226. The elongated hole 228 is sized and shaped such that the L-shaped tip may be easily passed therethrough when the stem 248 and tab 224 are in a second configuration, but is prevented from passing therethrough the stem 248 and tab 224 are rotated about a longitudinal axis thereof to a first configuration. The arms 234 extend from the clip body 232 to locking ends 238 which extend laterally inward to engage the recessed end 258 of the grooves 244.

The lock 202 is coupled to the body 204 such that the clip body 232 extends longitudinally within the longitudinal slot 242, the clip arms 234 extend through the grooves 244, and locking ends 238 of the clip arms 234 are received within the recessed ends 258 of the grooves 244. The clip 226 is connected to the tab 224 via the stem 248 which passes through the hole 228 and is positioned in the second configuration to prevent the tab 224 from being decoupled from the clip 226. The extension 252 of the tab 224 is received within the recess 250 surrounding the hole 228 to prevent the tab 224 and stem 228 from being rotated relative to the clip 226 and inadvertently moving the lock from the first configuration to the second configuration. In the locked configuration, clip 226 extends along a longitudinal axis and the engaging portion 212 thereof extends into the opening 206. The lock 202, however, may be moved to the unlocked configuration by pressing the tab 224 toward the proximal surface 220 of the body 204, bending the clip 226 out of alignment with the longitudinal axis to move the engaging portion 212 out of the opening 206. As described above, the arms 234 move within the grooves 244 to permit the clip 226 to be bent. The clip 226 may be formed of a material with elastic properties such as, for example, titanium, which biases the clip 226 in the locked configuration, but permits the clip 226 to be moved to the unlocked configuration. Thus, when it is desired to insert a device 214 such as a sleeve or other tool through the opening 206, a user may press the tab 224 to move the clip 226 to the unlocked configuration. When the device 214 is in the desired position within the opening 206, the tab 224 may be released to revert the clip 226 to the locked position, locking the device 214 therewithin.

Figure 16:
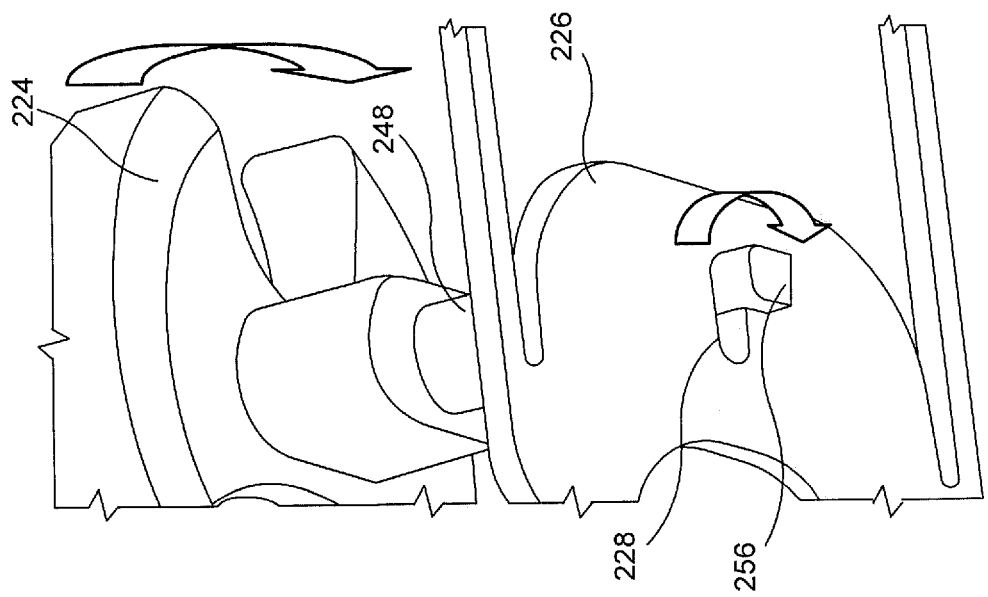
FIG. 16 shows a perspective view of the lock according to the device of FIG. 8.
Figure 15:
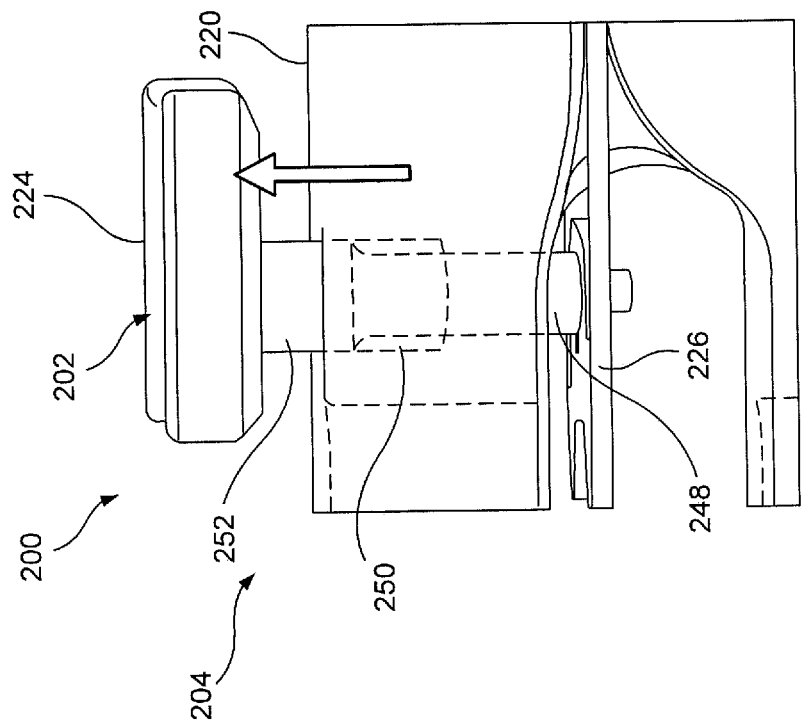
FIG. 15 shows a side view according to the device of FIG. 8.

Similarly to the device 100, the lock 202 may be decoupled from the body 204 so that the lock 202 and/or the body 204 may be cleaned and/or replaced, as needed. To decouple the lock 202 from the body 204, the tab 224 is pulled away from the proximal surface 220 of the body 204 until the extension 252 is removed from the recess 250, as shown in FIG. 15. The tab 224, and thereby the stem 248, may be rotated to move the lock 202 from the first configuration to the second configuration, to disengage the L-shaped tip 256 of the stem 248 from the hole 228 of the clip 226, as shown in FIG. 16. Once the tab 224 has been disengaged from the clip 226, the clip 226 may be easily removed from the body 204 by disengaging the locking ends 238 of the clip arms 234 from the locking recesses 258 since, as described above, the clip 226 is formed of an elastic material which permits the clip 226 to be bent as necessary.

Figure 17:
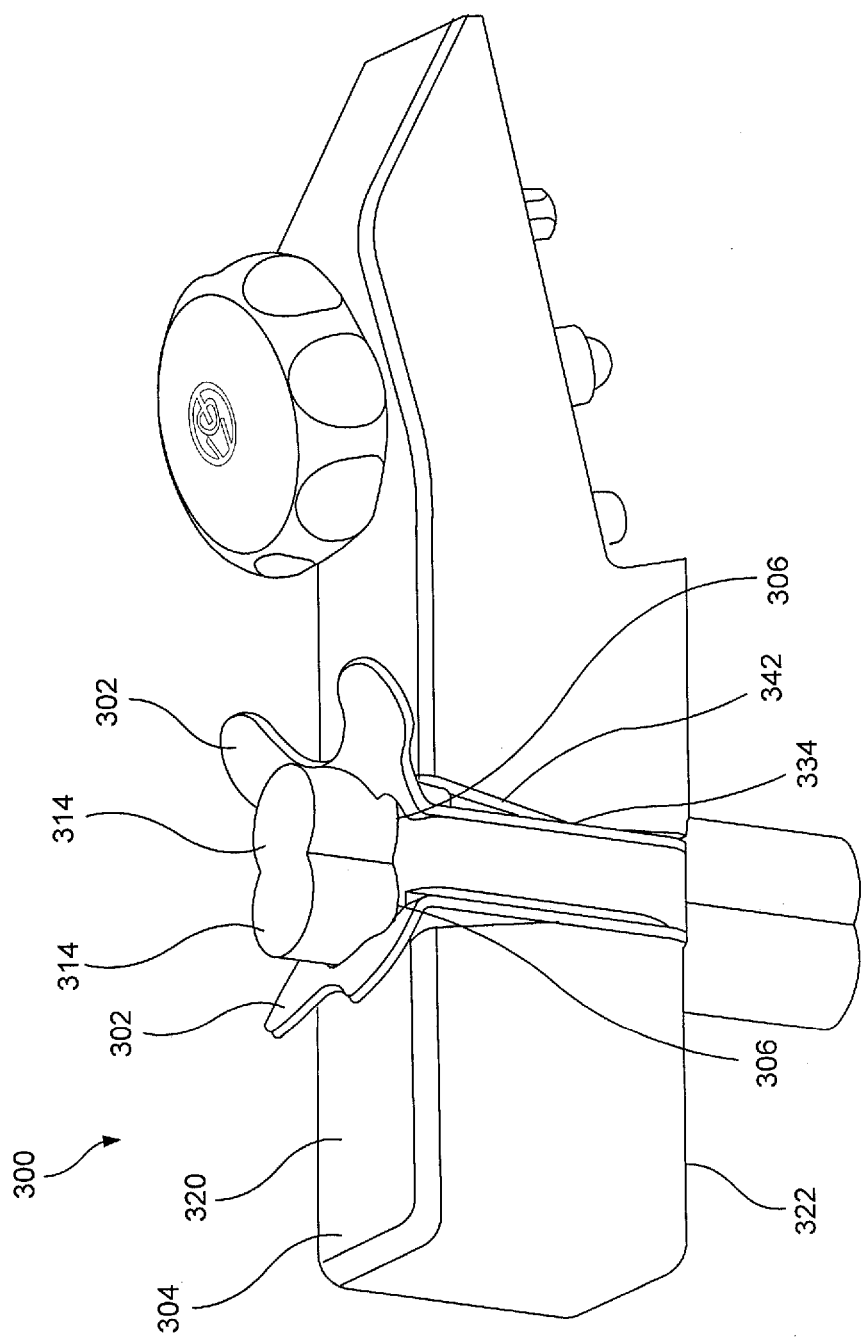
FIG. 17 shows a perspective view of an aiming device according to a third exemplary embodiment of the present invention.

As shown in FIGS. 17-18, an aiming device 300 according to a third exemplary embodiment of the present invention is substantially similar to the devices described above except as specifically noted below. The device 300 comprises a lock 302 coupled to a body 304 to lock a device 314 within an opening 306 of the body 304. Similarly to the clip 202, the clip 302 has resilient qualities and is biased in a locked configuration. Rather than extending longitudinally through the body 304, however, the lock 302 is a clip including arms 334 that extend laterally relative to a longitudinal axis of the body 304. As shown in FIG. 17, the body 304 includes grooves 342 extending laterally along lateral sides 346 on opposing sides of the opening 306. The grooves 342 are sized and shaped to receive the arms 334 of the lock therein and permit bending of the arms 334 therewithin.

As shown in FIG. 18, the lock 302 includes a tab 324 and a pair of arms 334 extending therefrom. The tab 324 may be sized and shaped to be easily gripped and/or pressed by a user of the device. An interior surface 332 of the tab 324 defines an engaging portion 312, which is sized and shaped to engage an outer surface of the device 314 such as a sleeve or other tool. The engaging portion 312 may, for example, include a curved recess for engaging a cylindrical device 314. The arms 334 are sized and shaped to be received within the grooves 342. Locking ends 338 of the arms 334 may extend laterally inward to engage, for example, locking recesses (not shown) of the grooves 342, similarly to the grooves 242 of the device 200. Alternatively, the locking ends 338 may engage a portion of the groove 342 along a distal surface 322 of the body 304. When the lock 302 is coupled to the body 304, the tab 324 extends proximally from a proximal surface 320 of the body 304 such that the lock 302 is accessible by the user. In one exemplary embodiment, the lock 302 may be formed of a spring steel such that the lock 302 is movable between the biased locked position and an unlocked configuration.

In the locked configuration, the lock 302 is biased such that the engaging portion 312 extends into the opening 306. To move the lock 302 to the unlocked configuration, the user presses the tab 324 toward the proximal surface 320 of the body 304, deforming the lock 302 to move the engaging portion 312 out of the opening 306. The user may move the lock 302 to the unlocked configuration to insert a device 314 into the opening 306. Once the device 314 has been inserted into the opening 306, as desired, the tab 324 may be released to permit the lock 302 to revert to the locked configuration, thereby locking the device 314 in the opening 306.

Similarly to the devices 100, 200 described above, the lock 302 may be decoupled from the body 304 to permit the lock 302 to be cleaned and/or replaced, as necessary. Since the lock 302 is formed of a resilient material, the arms 334 may simply be bent outward such that locking ends 338 of the arms 334 are disengaged from the groove 342.

As shown in FIGS. 19 and 20, an aiming device 400 according to another exemplary embodiment of the present invention is substantially similar to the aiming device 300 described above except as indicated below. The device 400 comprises a lock 402 coupled to a body 404 to lock a device within an opening 406 of the body 404. Similarly to the lock 302, the lock 402 includes a tab 424 and arms 434 which are biased toward a locked configuration. The lock 402 includes a tab 424 and a pair of arms 434 that extend laterally therefrom relative to a longitudinal axis of the body 404. The body 404 includes groves 442 extending along lateral sides 446 on opposite sides of the opening 406. The grooves 442 are sized and shaped to receive the arms 434. The arms 434, however, do not include locking ends extending radially inward to engage the body 404. Rather, the arms 434 are received within the grooves 442 and include ends 438 extending distally past a distal surface 422 of the body 404 and laterally outward. The ends 438 may be easily grasped by a user to draw the arms 434 away from one another to disengage the lock 402 from the body 404.

When the lock 402 is coupled to the body 404, as described above, the tab 424 extends over a proximal surface 420 of the body 404. In the locked configuration, the tab 424 is angled away from the proximal surface 420 and includes an engaging portion 412 such as, for example, a curved recess, which extends into a path of the opening 406. Thus, when a cylindrical device is passed through the opening 406, an outer surface thereof is engaged by the engaging portion 412. The tab 424 may be pressed toward a proximal surface of the 420 of the body 404 to move the device 400 to the unlocked configuration in which the engaging portion 412 is moved out of the path of the opening to release and/or permit insertion of a device through the opening 406.

In another substantially similar embodiment, also shown in FIGS. 19 and 20, a lock 424' is integrated into the body 404. Except as pointed out below, the lock 402' is substantially similar to the lock 402 comprising a tab 424' and arms 434' extending therefrom. The arms 434' of the lock 402' are received within holes 442' extending through the body 404 from a proximal surface 420 to a distal surface 422 thereof, on opposing sides of the opening 406. The lock 402' functions substantially similarly to the lock 402 described above, as an engaging portion 412' thereof is moved into and out of a path of the opening 406 to move the lock 402' between the locked and unlocked configurations, respectively. The body 404, however, further includes a recess 450 extending through the proximal surface 420. The recess 450 is sized and shaped to accommodate the tab 424', when the tab 424' is pressed toward the proximal surface 420 into the unlocked position. Although the aiming device 400 of FIGS. 19 and 20 shows both the lock 402 and the lock 402', it will be understood by those of skill in the art that the aiming device 400 may include one or both of the locks 402, 402'.

In another exemplary embodiment, as shown in FIGS. 21-22, an aiming device 500 is substantially similar to the aiming device 400 described above, except as pointed out below. The device 500 comprises a lock 502 coupled to a body 504 for movement relative thereto between a locked configuration in which a device passed through an opening 506 of the body 504 is locked therein and an unlocked configuration in which a device passed through body 504 is permitted to be moved therein. The lock 502 is biased toward the locked configuration and is formed of a wire bent to faun a tabbed portion 524 extending over a proximal surface 520 of the body 504 and arm portions 534 received within holes 542 extending through the body 504 from a proximal surface 520 to a distal surface 522 thereof, on opposing sides of the opening 506.

The tabbed portion 524 includes wire portions bent inward toward a centerline of the tabbed portion 524 to define an engaging portion 512 which, when the device 500 is in the locked configuration, extends into a path of the opening 506. Similarly to the device 400 described above, the tabbed portion 524 is angled away from the proximal surface 520 in the locked configuration. To move the lock 502 to the unlocked configuration, the tabbed portion 524 is pressed toward the proximal surface 520, into a recess 550 extending through proximal surface 520 and sized and shaped to accommodate the tabbed portion 524 therein. When the lock 502 is moved to the unlocked configuration, the engaging portion 512 is moved out of the path of the opening 506 such that a device such as an aiming sleeve may be freely moved into and out of the opening 506. Once the aiming sleeve has been positioned within the opening 506, as desired, the tabbed portion 524 may be released such that the engaging portion 512 (e.g., portions of the wire which have been bent inward toward the centerline thereof) engages an outer surface thereof and locks the sleeve therewithin.

Figure 23:
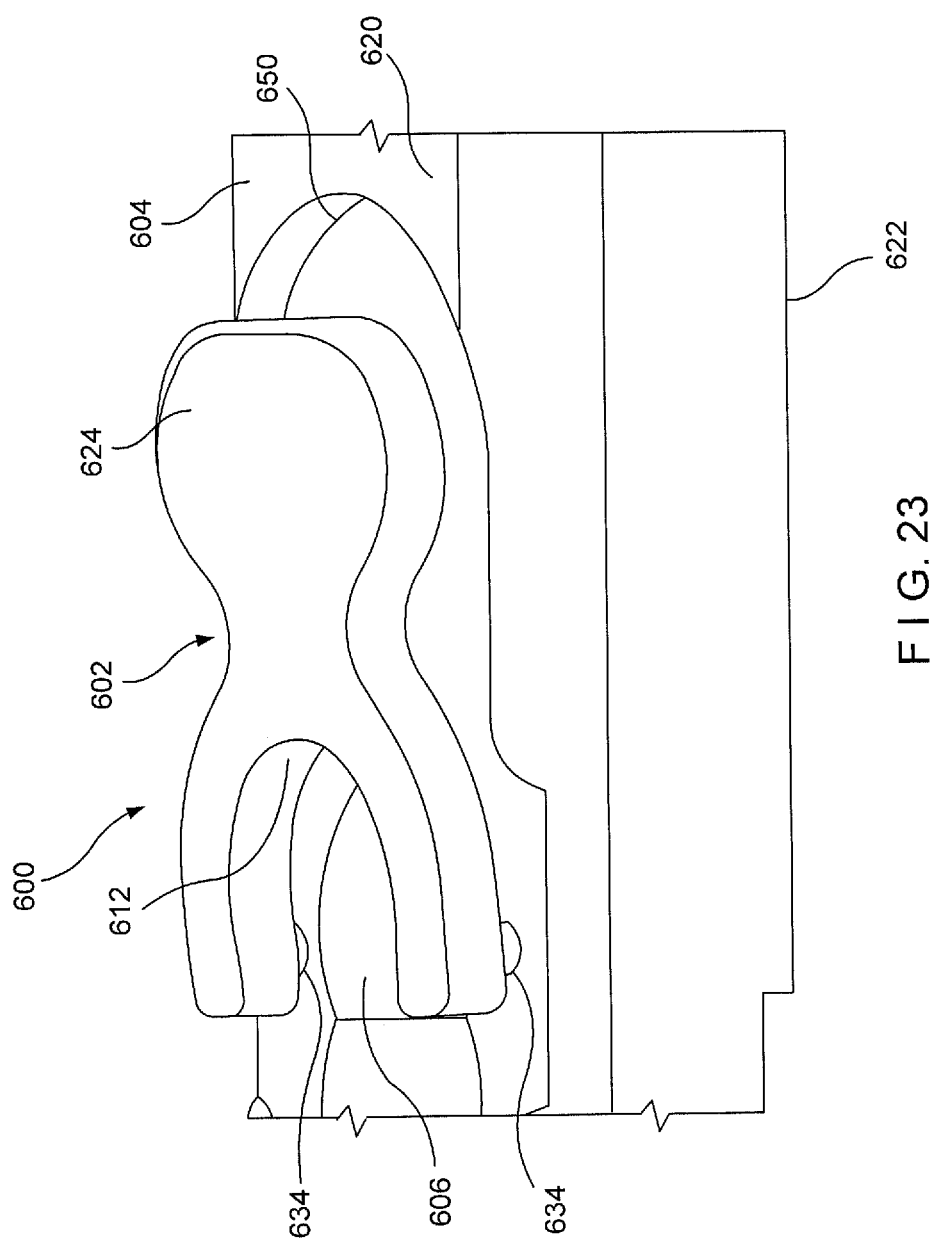
FIG. 23 shows a perspective view of a portion of an aiming device according to a sixth exemplary embodiment of the present invention.

As shown in FIGS. 23-24, an aiming device 600 according to yet another exemplary embodiment of the invention is substantially similar to the aiming device 400 except as described below. The device 600 comprises a lock 602 coupled to a body 604 for movement between a locked configuration, in which the lock 602 engages a sleeve or other tool passed through an opening 606 of the body 604 to lock the sleeve therein, and an unlocked configuration in which the sleeve or other tool is permitted to be movably passed into or out of the opening 606. The lock 602 includes a tab member 624 formed, for example, of a PEEK (polyether ether ketone) material connected to the body 604 via resilient pins 634 positioned within holes 642 extending through the body 604 from a proximal surface 620 to a distal surface 622 thereof on opposing sides of the opening 606 and acting as hinges which permit the lock 602 to be moved between the locked and unlocked configurations. In the locked configuration, for example, the pins 634 extend in a substantially straight configuration toward which they are biased. The pins 634 connect the tab member 624 to the body 604 such that an engaging portion 612 thereof extends into a path of the opening 606 and the tab member 624 is angled relative to a proximal surface 620 of the body 604. In the unlocked configuration, the pins 634 are deformed away from their biased position (e.g., curved) by pressing the tab member 624 toward the proximal surface 620 and moving the engaging portion 612 out of the path of the opening 606. The tab member 624 may be pressed into a recess 650 formed in the proximal surface 620, which is sized and shaped to receive the tab member 624 therein.

Those skilled in the art will understand that various modifications may be made to the invention without departing from the spirit or scope thereof. Thus, the present invention is intended to encompass all modifications and variations within the scope of the appended claims and their equivalents.

What is claimed is:

1. An aiming device, comprising:
   a body extending longitudinally from a first end to a second end and including a first body opening extending laterally therethrough along a first axis, the first body opening being sized and shaped to receive a device therein, the first end of the body including a coupling for coupling the body to an implantable device in an aiming configuration in which the first body opening is aligned with a corresponding first implant opening extending through the implantable device so that a device inserted through the first body opening in the body will pass along an axis of the first implant opening; and
   a lock releasably coupled to the body and movable relative thereto between an unlocked and a locked configuration, the lock including an engaging portion extending into the first body opening in the locked configuration to engage an outer surface of a device received therein to lock the device in a desired position within the first body opening.

2. The aiming device of claim 1, wherein the lock is coupled to the body via a pin such that the lock is pivotally movable between the unlocked and locked configurations.

3. The aiming device of claim 2, wherein the lock includes a tab extending laterally from a locking portion thereof, the locking portion pivotally received within a recess of the body extending longitudinally from the opening along a proximal surface thereof such that the tab extends proximally from the proximal surface in the unlocked configuration.

4. The aiming device of claim 3, wherein, in the locked configuration, the tab is movable toward the proximal surface to pivot the locking portion about the pin, moving the engaging portion into the first body opening.

5. The aiming device of claim 2, wherein the lock is coupled to the body via a pair of pins such that the lock is pivotally movable between the unlocked and locked configurations.

6. The aiming device of claim 1, wherein a width of the engaging portion is smaller than a width of a remaining portion of the locking portion.

7. The aiming device of claim 1, wherein the lock includes a clip biased toward the locked configuration.

8. The aiming device of claim 7, wherein the body includes a longitudinal slot extending longitudinally through the first body opening between proximal and distal surfaces of the body and a pair of opposing grooves extending along lateral surfaces of the body.

9. The aiming device of claim 8, wherein the clip includes a lock body received within the longitudinal slot and clip arms extending along the opposing grooves.

10. The aiming device of claim 7, wherein the lock further includes a tab connected to the clip such that when the tab is pressed toward a proximal surface of the body, the lock is moved to the unlocked configuration.

11. The aiming device of claim 10, wherein the tab is disengagable from the clip by rotating the tab relative to the clip to release the lock from the body.

12. The aiming device of claim 7, wherein body includes a pair of lateral grooves extending along lateral surfaces of the body on opposing sides of the first body opening to receive arms of the clip therein such that the engaging portion extends across a proximal surface of the body.

13. The aiming device of claim 7, wherein the clip is formed of one of titanium and spring steel.

14. The aiming device of claim 7, wherein the body includes a pair of holes extending therethrough from a proximal surface to a distal surface thereof on opposite sides of the first body opening to receive arms of the clip therein such that the engaging portion extends across the proximal surface of the body.

15. The aiming device of claim 7, wherein the clip is formed of a wire bent to include a tabbed portion defining the engaging portion, ends of the wire received within holes extending through the body from a proximal surface to a distal surface thereof on opposite sides of the first body opening such that the engaging portion extends across the proximal surface of the body.

16. The aiming device of claim 15, wherein the tabbed portion of the wire is bent inward toward a centerline of the tabbed portion to define the engaging portion.

17. The aiming device of claim 7, wherein the clip includes a tab member connected to the body via a pair of pins, which bias the clip toward the locked configuration, the tab member being connected to the body such that when the tab is pressed toward a proximal surface of the body, the pins are deformed and the lock is moved to the unlocked configuration.

18. An aiming device, comprising:
   a body extending longitudinally from a first end to a second end and including a first body opening extending laterally therethrough along a first axis, the first body opening being sized and shaped to receive a device therein, the first end of the body including a coupling for coupling the body to an implantable device in an aiming configuration in which the first body opening is aligned with a corresponding first implant opening extending through the implantable device so that a device inserted through the first body opening in the body will pass along an axis of the first implant opening; and
   a lock releasably coupled to the body and movable relative thereto between an unlocked and a locked configuration, the first body opening being unobstructed in the unlocked configuration to receive a device therein, the lock including an engaging portion extending into the first body opening in the locked configuration to engage an outer surface of a device received therein.

19. The aiming device of claim 18, wherein the lock is coupled to the body via a pin such that the lock is pivotally movable between the unlocked and locked configurations about the pin.

20. The aiming device of claim 18, wherein the lock includes a tab extending laterally from a locking portion thereof, the locking portion pivotally received within a recess of the body extending longitudinally from the opening along a proximal surface thereof such that the tab extends proximally from the proximal surface in the unlocked configuration.

21. The aiming device of claim 18, wherein the lock includes a clip biased toward the locked configuration.

22. The aiming device of claim 21, wherein the body includes a longitudinal slot extending longitudinally through the opening between proximal and distal surfaces of the body and a pair of opposing grooves extending along lateral surfaces of the body.

23. The aiming device of claim 22, wherein the clip includes a lock body received within the longitudinal slot and clip arms extending along the opposing grooves.

24. The aiming device of claim 21, wherein the lock further includes a tab connected to the clip such that when the tab is pressed toward a proximal surface of the body, the lock is moved to the unlocked configuration.

25. The aiming device of claim 24, wherein the tab is disengagable from the clip by rotating the tab relative to the clip to release the lock from the body.

26. The aiming device of claim 21, wherein body includes a pair of lateral grooves extending along lateral surfaces of the body on opposing sides of the first body opening to receive arms of the clip therein such that the engaging portion extends across the a proximal surface of the body.

27. The aiming device of claim 21, wherein the body includes a pair of holes extending therethrough from a proximal surface to a distal surface thereof on opposite sides of the first body opening to receive arms of the clip therein such that the engaging portion extends across the proximal surface of the body.

28. The aiming device of claim 21, wherein the clip is formed of a wire bent to include a tabbed portion defining the engaging portion, ends of the wire received within holes extending through the body from a proximal surface to a distal surface thereof on opposite sides of the first body opening such that the engaging portion extends across the proximal surface of the body.

29. The aiming device of claim 28, wherein the tabbed portion of the wire is bent inward toward a centerline of the tabbed portion to define the engaging portion.

30. The aiming device of claim 21, wherein the clip includes a tab member connected to the body via a pair of pins, which bias the clip in the locked configuration, the tab member connected to the body such that when the tab is pressed toward a proximal surface of the body, the pins are deformed and the lock is moved to the unlocked configuration.

31. The aiming device of claim 18, wherein the lock is coupled to the body via a pair of pins such that the lock is pivotally movable between the unlocked and locked configurations.

* * * * *